United States Patent [19]

Oren et al.

[11] Patent Number: 5,118,877
[45] Date of Patent: Jun. 2, 1992

[54] PROCESS FOR THE PREPARATION OF 2,3-DIMETHYLPHENOL AND OF 3,4-DIMETHYLPHENOL

[75] Inventors: Jakob Oren, Qiryak Bialik; Michael Zviely, Haifa; Joshua Hermolin, Ramat-Hasharon, all of Israel

[73] Assignee: Bromine Compounds Limited, Beer-Sheva, Israel

[21] Appl. No.: 639,523

[22] Filed: Jan. 10, 1991

[30] Foreign Application Priority Data

Jan. 12, 1990 [IL] Israel .................................. 93042

[51] Int. Cl.$^5$ ...................... C07C 37/01; C07C 37/02
[52] U.S. Cl. .................................................. 568/796
[58] Field of Search ............... 568/718, 296, 739, 716, 568/770

[56] References Cited

U.S. PATENT DOCUMENTS 2,085,429  6/1937  Hardierkwrhoff ................ 568/796
2,217,836 10/1940  Dierchs ............................. 568/796
3,352,927 11/1967  Vriel ................................. 568/796
4,891,452  1/1990  Nono et al. ...................... 568/796

Primary Examiner—Warren B. Lone
Attorney, Agent, or Firm—Michael N. Meller

[57] ABSTRACT

In a process for the preparation of mixtures of 2,3-dimethylphenol and 3,4-dimethylphenol a mixture of 2,3-dimethyl-bromobenzene and 3,4-dimethyl-bromobenzene is hydrolized in an aqueous alkaline solution in the presence of a copper compound catalyst of the formula:

$$Cu_{(n)}R_{(m)}$$

R represents —O or —OH or a residue of an inorganic or of an organic acid;
n is 1 or 2; and
m is 0, 1 or 2;

the reaction being carried out at a temperature in the range between 200° and 300° C.

17 Claims, No Drawings

PROCESS FOR THE PREPARATION OF 2,3-DIMETHYLPHENOL AND OF 3,4-DIMETHYLPHENOL

BACKGROUND OF THE INVENTION

1. The Field of the Invention

The present invention relates to a process for the preparation of 2,3-dimethylphenol and of 3,4-dimethylphenol. More particularly, the invention relates to a process in which the said compounds are prepared by hydrolysis of the corresponding bromobenzenes in an aqueous solution, to yield the desired product with high purity and yield.

2. The Prior Art

Dimethylphenols are useful intermediates in the synthesis of a variety of organic compounds, particularly in the preparation of polymers. Preparation of these compounds has been attempted by various routes in the art. For instance [FR 1,580,963; Czech Pat. 159,637; USSR 577202], sulphonation of xylene and subsequent hydrolysis has been carried out. In another process, xylene was brominated then aminated and diazotized. A diazo compound was decomposed to form the desired product [Z. N. Lavrova et al, C.A. 76: 33912w (1972)]. Alternative methods employed were the nitration of xylene [C.A. 70: 106432c (1969)], the oxidation of xylene with a peroxide [U.S. Pat. No. 3,377,386] and the hydrolysis of 3,4-dimethylanisole [C.A. 52: 14563d (1958)].

However, the processes of the art present several disadvantages. For instance, sulphonation is a less selective process than bromination, and hydrolysis thereof must be carried out under conditions which are more extreme than those required for the hydrolysis of bromides (usually at temperatures higher than 300° C. and for relatively longer periods of time). Aminating and then diazotizing, on the other hand, is not a convenient procedure because one extra step, as compared with the hydrolysis route, is required, and diazotization normally results in lower yields than hydrolysis. Nitration is a relatively non-selective reaction, which leads to considerable waste of by-products.

It is therefore clear that it would be highly desirable to provide a simple, efficient and highly specific process which overcomes the drawbacks of the processes of the present art.

SUMMARY OF THE INVENTION

It has now been found, and this is an object of the present invention, that it is possible to hydrolize a mixture of 2,3-dimethyl-bromobenzene and 3,4-dimethylbromobenzene in an aqueous solution, and to obtain a crude product which can then be easily purified to give a pure 2,3-dimethylphenol and 3,4-dimethylphenol in high yields.

As will be apparent to a person skilled in the art, the process of the invention leads to considerable economic advantages. Bromoxylenes can be easily obtained by the direct bromination of xylene, which will typically yield 3-isomer: 4-isomer ratios of 15:85, or by the bromination of xylene in SO$_2$, which will lead to mixtures such as 5% 3-isomer: 95% 4-isomer. It is not known, however, to prepare pure 3- or 4-isomer by a selective bromination. Furthermore, separating the two bromo-isomers, which are very similar in chemical and physical properties, is difficult and expensive. Therefore, the ability to employ mixtures of these isomers which have been obtained by a simple bromination step, without the need for expensive separations, considerably simplifies the process and renders it considerably more economic.

It is clear, however, that if a pure isomer is previously made available, it can be reacted in the same way in which mixtures of the two isomers are reacted.

The process according to the invention is thus directed to the preparation of pure 2,3-dimethylphenol and 3,4-dimethylphenol, and comprises hydrolyzing a mixture of 2,3-dimethyl-bromobenzene and 3,4-dimethylbromobenzene, in an aqueous alkaline solution in the presence of a copper compound catalyst of the formula:

$$Cu_{(n)}R_{(m)}$$

wherein:
R represents —O or —OH or a residue of an inorganic or of an organic acid;
n is 1 or 2; and
m is 0, 1 or 2;
the reaction being carried out at a temperature in the range between 200° and 300° C.

The ratio of the two isomers may be any available ratio, as it affects only the product distribution.

As will be easily understood by a person skilled in the art, and as will be illustrated in the following example, it will often be desired to provide not only the mixture of the final compounds as detailed above, but also the pure isolated final compounds. Thus, the invention is also directed to a process for the simultaneous preparation of substantially pure 2,3-dimethylphenol and of substantially pure 3,4-dimethylphenol, which process comprises the steps of:

Preparing a mixture of the said compounds by hydrolizing a mixture of 2,3-dimethyl-bromobenzene and 3,4-dimethyl-bromobenzene of any available isomer ratio, in an aqueous alkaline solution in the presence of a copper compound catalyst of the formula:

$$Cu_{(n)}R_{(m)}$$

wherein:
R represents —O or —OH or a residue of an inorganic or of an organic acid;
n is 1 or 2; and
m is 0, 1 or 2;
the reaction being carried out at a temperature in the range between 200° and 300° C.;
Separating the copper compound catalyst and if desired, recycling same to another reaction batch;
Neutralizing or acidifying the reaction mixture to obtain phase separation;
Separating the organic and the aqueous phases;
If necessary, extracting the remaining product from the aqueous phase with an organic extraction solvent;
Evaporating the organic solvent; and
Separating 2,3-dimethylphenol from 3,4-dimethylphenol by fractional distillation of the organic phase.

According to a preferred embodiment of the invention, the aqueous solution is made alkaline by the addition of NaOH or of KOH, or of mixtures thereof, although the active nature of the alkaline compound is important only inasmuch as it obtains the required pH. Preferably, the total amount of alkali added is between 2 and 5 equivalents of the bromine found in the starting material.

The reaction can be carried out in a wide range of temperatures. However, temperatures below 200° C. are not preferred because the reaction rates obtained thereby are selectively slow. The preferred, but not limiting reaction temperature will be between 200° and 300° C. Temperatures above 300° C. are normally not preferred, as they lead to increased autoclave pressures and may lead to undesirable by-products. It should be kept in mind that, in order to maintain the temperature, the reaction will preferably be carried out in a sealed vessel under autogenous pressure. It should likewise be emphasized that stirring is an important factor in the progress of the reaction, and efficient stirring is necessary for obtaining a fast and complete conversion of the starting material. The reaction can be carried out in a batch, semicontinuous or continuous mode.

As said, the reaction is carried out in the presence of a copper catalyst. The actual nature of the copper catalyst is not important, as long as it is compatible with the reaction system, and a variety of catalysts can be employed. Examples of representative catalysts of this type are $CuSO_4$, $CuO$, $Cu_2O$, $CuBr$, $CuBr_2$, $Cu(OH)_2$, $CuCl$, $CuCl_2$ and their mixtures. The copper catalyst is suitably present in the reaction medium in an amount of between 0.1–10% by mole of the bromoxylenes, preferably in an amount comprised between 2–7% by mole. As said, the catalyst is separated during work-up and can be recycled.

At the end of the reaction, as stated above, the pH of the reaction mixture is lowered by adding any suitable acid, preferably a strong acid such as HCl. Acidification of the reaction mixture is effected in order to neutralize the phenoxides and obtain phase separation. Preferably, the pH of the reaction mixture will be lowered to a value of 9 or less.

Some xylene may be formed through minor hydrogenolysis of the bromo-compounds. However, this formation does not lead to any technological complication, as the xylene formed is easily removed with the solvent and recycled to the bromination stage. Xylene may also be conveniently used as the medium for the extraction of the residues of the product in the aqueous phase, if such extraction is carried out.

All the above and additional characteristics and advantages of the process of invention will now be further illustrated through the following non-limitative examples thereof.

EXAMPLE 1

Into a 0.5 liter SS-316 autoclave, there were added 92.5 g (0.5 mole) of a mixture of 2,3-dimethyl-bromobenzene and 3,4-dimethyl-bromobenzene (1:5 ratio), 280 g aqueous 20% NaOH (1.4 mole) and 2.5 g CuCl (0.025 mole). The autoclave was sealed and heated to 250° C. Full conversion was achieved after two hours. The autoclave was cooled, opened and the reaction mixture was filtered to recover the catalyst. The mixture was neutralized to pH 5 with concentrated HCl and two phases separated. The organic phase contained 55 g product (a mixture of 2,3-dimethylphenol and 3,4-dimethylphenol, 1:5 ratio). Extraction of the aqueous phase with ethyl acetate produced another 1.5 g of the same mixture of products. The overall yield exceeded 90% and no change in the original ratio of isomers could be detected. After evaporation of the volatiles, the mixture could be separated into its pure ($\geq 99\%$) components by means of fractional distillation.

EXAMPLE 2

Example 1 was repeated on a mixture of 2,3-dimethyl-bromobenzene and 3,4-dimethyl-bromobenzene in a ratio of 1:15.

The same yield of product, 2,3-dimethyl phenol and 3,4-dimethyl phenol, was obtained, also in a ratio of 1:15.

EXAMPLES 3–7

Example 1 was repeated under various conditions, which are summarized in the following table:

TABLE I

| Hydrolysis of a mixture of dimethyl-bromobenzenes (BX) | | | | | | |
|---|---|---|---|---|---|---|
| Example No. | Reagents (moles) | | | Temp. deg. C. | Time hrs. | Conversion % |
| | BX | 20% NaOH | CuCl | | | |
| 3 | 0.3 | 1.2 | 0.020 | 250 | 2.0 | 100 |
| 4 | 0.5 | 1.0 | 0.025 | 250 | 2.0 | 100 |
| 5 | 0.5 | 1.5 | 0.025 | 240 | 2.5 | 100 |
| 6 | 0.3 | 1.2 | 0.020 | 220 | 3.5 | 96 |
| 7 | 0.5 | 1.5 | 0.002 | 240 | 3.0 | 67 |

EXAMPLES 8–11

The following catalysts were tested under the conditions described in Example 1:

TABLE II

| Example No. | Catalyst |
|---|---|
| 8 | CuO |
| 9 | CuBr |
| 10 | $CuSO_4 \cdot nH_2O$ |
| 11 | Recycled Catalyst (from Example 1) |

The results obtained were substantially identical to those obtained in Example 1.

We claim:

1. A process for the preparation of mixtures of 2,3-dimethylphenol and 3,4-dimethylphenol comprising hydrolyzing a mixture of 2,3-dimethyl-bromobenzene and 3,4-dimethyl-bromobenzene, in an aqueous alkaline solution in the presence of a copper compound catalyst of the formula:

$$Cu_{(n)}R_{(m)}$$

wherein:
R represents —O or —OH or a residue of an inorganic or of an organic acid;
n is 1 or 2; and
m is 0, 1 or 2;
the reaction being carried out at a temperature in the range between 200° and 300° C.

2. A process for the simultaneous preparation of substantially pure 2,3-dimethylphenol and of substantially pure 3,4-dimethylphenol comprising the steps of:
Preparing a mixture of the said compounds by the process of claim 1;
Separating the copper compound catalyst;
Neutralizing or acidifying the reaction mixture to obtain phase separation;
Separating the organic and the aqueous phases;
optionally, extracting the remaining product from the aqueous phase with an organic extraction solvent, evaporating the solvent; and separating 2,3-dimethylphenol from 3,4-dimethylphenol by fractional distillation of the organic phase(s).

3. A process according to claim 1, wherein the aqueous solution is made alkaline by the addition of NaOH or KOH or mixtures thereof.

4. A process according to claim 3, wherein the total amount of alkali added is between 2 and 5 equivalents of the halogen in the starting material.

5. A process according to claim 1, wherein the reaction temperature is in the range between 200° and 300° C.

6. A process according to claim 1, wherein the copper catalyst is selected from among $CuSO_4$, CuO, $Cu_2O$, CuBr, $CuBr_2$, $Cu(OH)_2$, CuCl, $CuCl_2$ and their mixtures.

7. A process according to claim 6, wherein the copper catalyst is present in an amount of between 0.1-10% by mole, preferably between 2-7% by mole.

8. A process according to claim 2, wherein the pH of the product mixture is lowered to a value of 9 or less.

9. A process according to claim 2, wherein the extraction solvent is xylene.

10. A process according to claim 1, wherein the copper compound catalyst is a catalyst recycled from a previous reaction.

11. A process according to claim 2, wherein the aqueous solution is made alkaline by the addition of NaOH or KOH or mixtures thereof.

12. A process according to claim 11, wherein the total amount of alkali added is between 2 and 5 equivalents of the halogen in the starting material.

13. A process according to claim 2, wherein the reaction temperature is in the range between 200° and 300° C.

14. A process according to claim 3, wherein the reaction temperature is in the range between 200° and 300° C.

15. A process according to claim 2, wherein the copper catalyst is selected from among $CuSO_4$, CuO, $Cu_2O$, CuBr, $CuBr_2$, $Cu(OH)_2$, CuCl, $CuCl_2$ and their mixtures.

16. A process according to claim 15, wherein the copper catalyst is present in an amount of between 0.1-10% by mole, preferably between 2-7% by mole.

17. A process according to claim 2, wherein the copper compound catalyst is a catalyst recycled from a previous reaction.

* * * * *